US010828438B2

(12) United States Patent
Thompson et al.

(10) Patent No.: US 10,828,438 B2
(45) Date of Patent: Nov. 10, 2020

(54) ELECTRONIC APPARATUS CONTROL USING A BREATHING ASSISTANCE APPARATUS

(75) Inventors: James Malcolm Thompson, Auckland (NZ); Fiona Elizabeth Cresswell, Auckland (NZ); Donald Roy Kuriger, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 468 days.

(21) Appl. No.: 14/110,083

(22) PCT Filed: Mar. 7, 2012

(86) PCT No.: PCT/NZ2012/000034
§ 371 (c)(1),
(2), (4) Date: Dec. 16, 2013

(87) PCT Pub. No.: WO2012/138233
PCT Pub. Date: Oct. 11, 2012

(65) Prior Publication Data
US 2014/0116440 A1 May 1, 2014

Related U.S. Application Data

(60) Provisional application No. 61/473,081, filed on Apr. 7, 2011.

(51) Int. Cl.
*A61M 16/00* (2006.01)
*A61B 5/087* (2006.01)
(Continued)

(52) U.S. Cl.
CPC ....... *A61M 16/0051* (2013.01); *A61B 5/0476* (2013.01); *A61B 5/087* (2013.01);
(Continued)

(58) Field of Classification Search
CPC ..... A61M 16/00–0012; A61M 16/0051–0075; A61M 16/16–168;
(Continued)

(56) References Cited

U.S. PATENT DOCUMENTS

| 6,290,654 B1 * | 9/2001 | Karakasoglu | A61B 5/087 |
| | | | 128/201.23 |
| 6,397,845 B1 * | 6/2002 | Burton | A61M 16/00 |
| | | | 128/204.18 |

(Continued)

FOREIGN PATENT DOCUMENTS

| DE | 33 38 649 A1 | 5/1985 |
| EP | 2 263 530 A1 | 12/2010 |

(Continued)

OTHER PUBLICATIONS

EPO Search Report; dated Aug. 21, 2014; 8 pages.

(Continued)

*Primary Examiner* — Samchuan C Yao
*Assistant Examiner* — Ned T Heffner
(74) *Attorney, Agent, or Firm* — Knobbe, Martens, Olson & Bear, LLP (57) ABSTRACT

A breathing gases supply apparatus 1 can comprise a blower 103/105 and breathing circuit for delivering breathing gases to a patient. The apparatus also can comprise a first controller 109, the controller 109 configured to receive input from at least one sensor 110-112 indicative of patient breathing, and a transmitter 201 configured to communicate with the controller 109 and transmit control signals to an electronic apparatus 203. The controller 109 can be configured to determine sleep in a patient based on the occurrence of a breathing pattern indicative of sleep, detected from the input received from the sensor 110-112 and upon determin- (Continued)

ing sleep, operate the transmitter 201 to send a control signal to control an electronic apparatus 203.

19 Claims, 5 Drawing Sheets

(51) Int. Cl.
*A61B 5/00* (2006.01)
*A61M 16/16* (2006.01)
*A61M 21/02* (2006.01)
*A61B 5/0476* (2006.01)
*A61M 21/00* (2006.01)
*A61M 16/10* (2006.01)

(52) U.S. Cl.
CPC .......... *A61B 5/4812* (2013.01); *A61B 5/4818* (2013.01); *A61B 5/4836* (2013.01); *A61B 5/746* (2013.01); *A61M 16/0066* (2013.01); *A61M 16/0069* (2014.02); *A61M 16/024* (2017.08); *A61M 16/16* (2013.01); *A61M 16/161* (2014.02); *A61M 21/02* (2013.01); *A61B 2562/0204* (2013.01); *A61B 2562/029* (2013.01); *A61B 2562/0219* (2013.01); *A61B 2562/0247* (2013.01); *A61M 16/109* (2014.02); *A61M 2016/0027* (2013.01); *A61M 2016/0039* (2013.01); *A61M 2021/0083* (2013.01); *A61M 2205/18* (2013.01); *A61M 2205/3317* (2013.01); *A61M 2205/3334* (2013.01); *A61M 2205/3375* (2013.01); *A61M 2205/3561* (2013.01); *A61M 2205/3584* (2013.01); *A61M 2205/50* (2013.01); *A61M 2230/005* (2013.01); *A61M 2230/10* (2013.01); *A61M 2230/63* (2013.01); *F04C 2270/0421* (2013.01)

(58) Field of Classification Search
CPC ... A61M 16/20–207; A61M 2016/0015–0042; G01F 1/00; G05D 7/00; A61B 5/00; A61B 5/0004; A61B 5/0006; A61B 5/0476; A61B 5/082; A61B 5/0823; A61B 5/0826; A61B 5/087–097; A61B 5/48; A61B 5/4806–4818
See application file for complete search history.

(56) References Cited

U.S. PATENT DOCUMENTS

| | | | |
|---|---|---|---|
| 7,798,144 B2 | 9/2010 | Kwok et al. | |
| 7,896,812 B2 | 3/2011 | Rapoport et al. | |
| 7,956,755 B2 | 6/2011 | Lee et al. | |
| 2001/0044588 A1* | 11/2001 | Mault | A61B 5/0002 600/549 |
| 2005/0076906 A1* | 4/2005 | Johnson | A61M 16/0051 128/204.21 |
| 2005/0235993 A1 | 10/2005 | Baecke et al. | |
| 2006/0064037 A1* | 3/2006 | Shalon | A61B 5/0006 600/586 |
| 2006/0231097 A1* | 10/2006 | Dougherty et al. | A61M 16/00 128/204.18 |
| 2007/0023044 A1* | 2/2007 | Kwok | A61M 16/0057 128/204.23 |
| 2007/0023045 A1* | 2/2007 | Kwok | A61M 16/0057 128/204.23 |
| 2007/0118026 A1 | 5/2007 | Kameyama et al. | |
| 2008/0306330 A1 | 12/2008 | Lindback et al. | |
| 2009/0149699 A1 | 6/2009 | Ullmann | |
| 2010/0094103 A1 | 4/2010 | Kaplan | |
| 2010/0125218 A1 | 5/2010 | Haartsen et al. | |
| 2010/0145167 A1 | 6/2010 | Im | |
| 2011/0010014 A1 | 1/2011 | Oexman et al. | |

FOREIGN PATENT DOCUMENTS

| | | |
|---|---|---|
| WO | WO 2004/032719 A2 | 4/2004 |
| WO | WO 2006/133493 A1 | 12/2006 |
| WO | WO 2011/006199 A1 | 1/2011 |

OTHER PUBLICATIONS

International Search Report; PCT/NZ2012/000034; dated Jun. 22, 2012, 4 pages.
Written Opinion; PCT/NZ2012/000034; dated Jun. 22, 2012; 6 pages.
Extended European Search Report dated Feb. 5, 2020 in related EP Application No. 19192099.

\* cited by examiner

ELECTRONIC APPARATUS CONTROL USING A BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present invention relates to a breathing assistance apparatus and a method implemented by a breathing assistance apparatus (breathing gases supply apparatus) for remotely controlling electronic apparatus such as home appliances or electronics. The breathing apparatus could be, for example, a PAP apparatus.

Description of the Related Art

Respiratory disorders affect the ability of a sufferer to breathe. One treatment of respiratory disorder involves delivering pressurised breathing gases to a person experiencing the disorder. A common respiratory disorder is an apnea. Apneas are caused by the collapse of the muscles supporting a person's airways during sleep, resulting in a partial or complete blockage of the breathing passages. This is commonly known as Obstructive Sleep Apnea (OSA). Other events such as hypopneas and restricted breathing (flow limitations) also fall into the broad category of sleep disorder breathing (SDB) events. A hypopnea involves episodes of overly shallow breathing or an abnormally low respiratory rate. Restricted breathing is caused by a restriction in the person's airway most commonly caused by the person's airway partially closing. These events (that is, SDB events) also occur during sleep and cause a person to wake mid sleep, and can limit the amount of sleep a person can get.

SDB events are commonly treated using Positive Airway Pressure (PAP) therapy. PAP involves delivering breathing gases at a pre-determined pressure above atmospheric to the patient. The raised pressure breathing gases force the user's airways open to maintain a substantially unrestricted breathing passage. The predetermined pressure at which treatment is delivered is generally determined by clinical trials prior to regular treatment. In particular Continuous Positive Airway Pressure (CPAP) therapy is used to treat SDB events. In basic CPAP therapy the pressure is constantly maintained at a predetermined pressure. There are other PAP therapies like Bi level PAP and auto CPAP in which there is a high positive pressure at inspiration and a lower pressure at expiration is delivered to maintain open airways.

PAP therapy is delivered to a patient by a treatment system for delivering breathing gases to the patient. The system typically includes a flow generator for generating a flow of gases, a conduit to transport the breathing gases generated by the flow generator, and a patient interface to deliver the gases to the patient. The system may include a humidifier to humidify the breathing gases prior to delivering the gases to a user.

PAP treatment systems are generally used in the home by a user. PAP treatment systems are used by a person or patient during sleep to prevent SDB events such as OSA and sometimes provide inspiratory assistance, as is the case for bi-level PAP. However PAP treatment systems are also utilised by a person when the person is awake and preparing for sleep. The treatment system continues to operate after the person has fallen asleep.

SUMMARY OF THE INVENTION

Quite often the user or person is watching TV or listening to the radio or has other appliances or electrical apparatuses operating while the user is using a PAP treatment system. As the user falls asleep these appliances may remain switched on without the user realising. For example, the user may be watching TV, utilising the PAP treatment system and falls asleep and the TV continues to run throughout the night causing excessive power use. Another example is the user may be in bed or on the couch using the PAP treatment system and falls asleep while the lights remain on throughout the night. This is again disadvantageous because it causes higher power consumption.

It is an object of the present invention to control an electronic apparatus using a breathing gases supply apparatus or at least provide the public with a useful choice.

The terms "sleep" and "asleep" as used in this specification are intended to encompass a) the onset of sleep, b) an actual sleep state where the patient is asleep (such as the REM sleep state and the non-REM sleep state), or c) a change in sleep state, for example from non-REM sleep to REM sleep or any other such sleep state change. A change in sleep state can also be considered the onset of sleep, going from a non-sleep state to a sleep state.

In one aspect the present invention may be said to consist in a breathing gases supply apparatus comprising: a blower and breathing circuit for delivering breathing gases to a patient, a first controller, the controller configured to receive input from at least one sensor indicative of patient breathing, a transmitter configured to communicate with the controller and transmit control signals to an electronic apparatus, wherein the controller is configured to determine sleep in a patient based on the occurrence of a breathing pattern indicative of sleep, detected from the input received from the sensor and upon determining sleep, operate the transmitter to send a control signal to control an electronic apparatus.

Preferably the sensor measures breath flow of a patient.

Preferably the breathing pattern indicative of sleep is a sleep disorder breathing (SDB) event.

Preferably the breathing pattern indicative of sleep is a rhythmic or erratic breathing pattern, or a change between a rhythmic or erratic breathing pattern.

Preferably the breathing gases supply apparatus comprises a PAP apparatus.

Preferably the apparatus further comprises at least one sensor.

Preferably the sensor is any one or more of the following: flow sensor, pressure sensor, humidity sensor, sound sensor (such as a microphone), mass flow sensor, voltage sensor, current sensor, sensor or sensors to determine the state of the electronic apparatus, EEG sensor, position sensor, or accelerometer Preferably the first controller is further configured to control the blower and breathing circuit.

Preferably the first controller is integrated in the breathing gases supply apparatus.

Preferably the first controller is removable from the breathing gases supply apparatus.

Preferably the first controller is remote from and communicates with the breathing gases supply apparatus.

Preferably the breathing gases supply apparatus further comprises a second controller configured to control the blower and breathing circuit.

Preferably the first or second controller is configured to control the usual operations of the apparatus based on the input from at the sensor indicative of patient breathing, and/or from the determined breathing pattern indicative of sleep.

Preferably either the first controller or second controller is configured to determine sleep based on the any one or more of the following: number of SDB events, duration of SDB events, spread of SDB events, and types of SDB events.

Preferably the SDB event is one or more of a flow limitation, hypopnea or apnea.

Preferably the control signal changes the state of the electronic apparatus.

Preferably the control signal switches off an electronic apparatus.

Preferably the transmitter utilises infrared, RF or sonic energy to send the control signal.

Preferably the electronic apparatus is further configured to transmit a signal to the controller and the controller further configured to receive the signal from the electronic apparatus.

Preferably the electronic apparatus is one or more of a: television, radio, lights, heater, air conditioner, heat pump, media player.

In another aspect the present invention may be said to consist in a method for controlling an electronic apparatus using a breathing gases supply apparatus for delivering breathing gases to a patient, the method comprising the steps of: obtaining input indicative of a patient's breathing, determining sleep in a patient based on the occurrence of a breathing pattern indicative of sleep from the input, upon determining sleep, operating a transmitter to send a control signal to control an electronic apparatus.

Preferably the input is indicative of the breath flow of a patient.

Preferably the breathing pattern indicative of sleep is a sleep disorder breathing (SDB) event.

Preferably the breathing pattern indicative of sleep is a rhythmic or erratic breathing pattern, or a change between a rhythmic or erratic breathing pattern.

Preferably the sensor is any one of the following: flow sensor, pressure sensor, humidity sensor, sound sensor (such as a microphone), mass flow sensor, voltage sensor, current sensor, sensor or sensors to determine the state of the electronic apparatus, EEG sensor.

Preferably the first controller or second controller is configured to determine sleep based on the one or more of the: number of SDB events, duration of SDB events, spread of SDB events, types of SDB events.

Preferably the SDB event being any one of a flow limitation, hypopnea or apnea.

Preferably the control signal is sent using infrared, RF or sonic energy.

Preferably the electronic apparatus is one or more of: television, radio, lights, heater, air conditioner, heat pump, media player, alarm device (such as an alarm clock).

Preferably the control signal changes the state of the electronic apparatus.

Preferably the control signal switches off or on the electronic apparatus.

Preferably the input indicative of patient's breathing is further used to control the breathing gases supply apparatus.

Preferably the method further comprising the step of: determining the current state of an electronic apparatus when the PAP apparatus is switched on to deliver breathing gases.

In another aspect the present invention may be said to consist in a breathing gases supply apparatus comprising: a blower and breathing circuit for delivering breathing gases to a patient, a first controller, the controller configured to receive input from at least one sensor indicative of patient breathing, a transmitter configured to communicate with the controller and transmit control signals to an alarm device, wherein the controller is configured to determine a sleep state in a patient and operate the transmitter to send a control signal to activate the alarm of an alarm device when a desired time is reached and the patient is in a sleep state conducive to being woken.

In another aspect the present invention may be said to consist in a method for controlling an alarm device using a breathing gases supply apparatus for delivering breathing gases to a patient, the method comprising the steps of: determining a sleep state in a patient, upon reaching a desired time and determining a sleep state conducive to being woken, operating a transmitter to send a control signal to control an electronic apparatus.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE PREFERRED EMBODIMENT

Overview

The present invention provides a method and apparatus for controlling an electronic apparatus such as a home appliance, using a PAP apparatus or other breathing assistance apparatus (breathing gases supply apparatus). The present invention also relates to a PAP apparatus that can control an electronic apparatus. The occurrence of an SDB event or other event or pattern of breathing indicative of sleep determined by the PAP apparatus can serve as an indicator that the person is asleep, and can be used as a trigger to control an electronic apparatus. As noted earlier, the terms "asleep" and "sleep" should be interpreted broadly and can cover various sleep states comprising the onset of sleep, actual sleep and also a change in sleep state. So the SDB or other event or pattern of breathing indicative of sleep can serve as an indicator of actual sleep, and/or onset of sleep or change in sleep state. Any of these types of sleep, once detected can be used to trigger to control an electronic apparatus.

An electronic apparatus can be interpreted generally to cover any type of electrical or electronic equipment such as home appliances and/or other electrical/electronic devices. For example, an electronic apparatus could be one or more of a: television, radio, light, heater, air conditioner, heat pump, media player, alarm device (such as an alarm clock).

In one embodiment, a PAP apparatus is configured to measure data or parameters indicative of a patient's breathing (such as breath flow data/parameters or pressure data/parameters), determine the occurrence of an SDB event or other sleep indicative breathing pattern (e.g. sleep indicative breathing characteristic) in a controller/control system, from that determine sleep in the person (e.g. if the person is actually asleep, has reached onset of sleep or has changed sleep state), and control one or more electronic apparatus based on the determination.

Common breathing patterns indicative of sleep are SDB events, which comprise apneas, hypopneas and flow restrictions in the airways. Other breathing patterns detected or determined can be a lower tidal volume, a lower breath rate, lack of variability or a change in pulse rate. Any one or more or a combination of one or more changes listed above can be detected or determined by the system. Such changes in the breathing result in a breathing pattern indicative of sleep. Breathing characteristics that may be indicative of sleep, and are detected or determined by the controller are tidal volumes breathing rates, pulse rates and variability in breathing. Any one or more of these or a combination of these can be indicative of sleep.

In general, the PAP apparatus can from the flow or pressure data/parameters determine any patterns that indicate sleep, and from that trigger control of an electronic apparatus.

Breathing Apparatus

Figure 1:
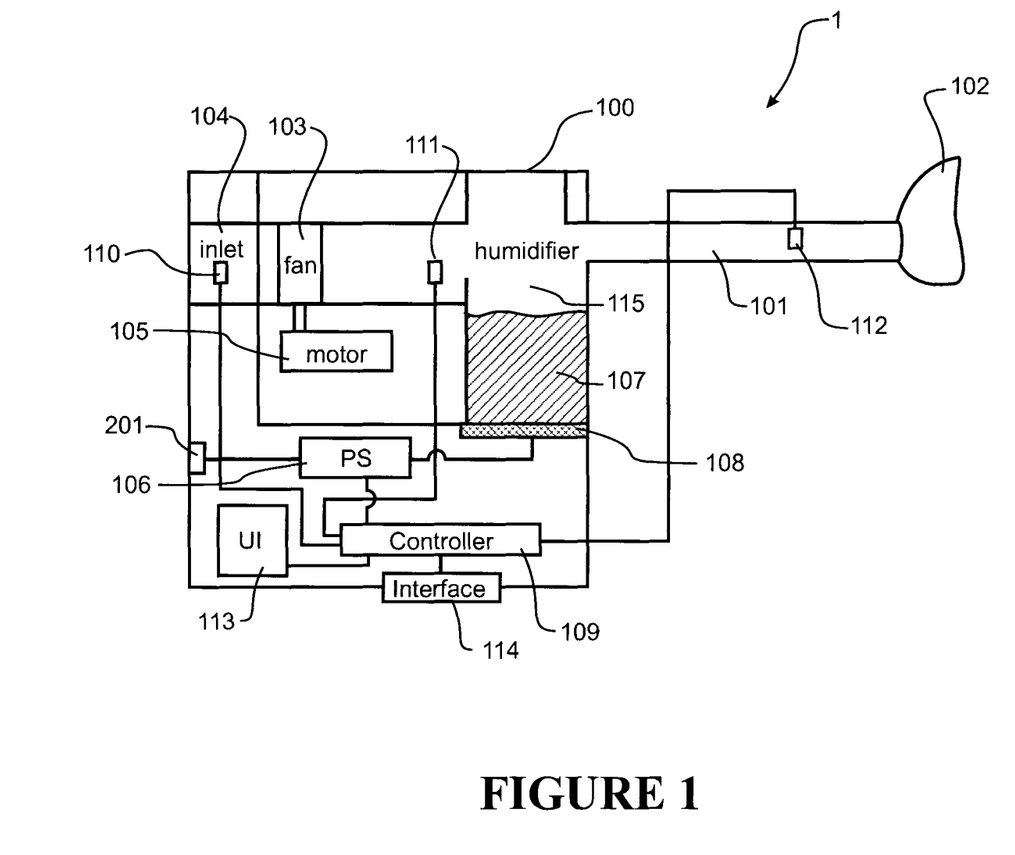
FIG. 1 is a block diagram illustrating a gas supply device for implementing or performing the present invention.

FIG. 1 is a block diagram illustrating one embodiment of a breathing gases supply system/apparatus 1 incorporating the present invention. The full system comprises a PAP apparatus 100 for delivering a supply of breathing gases, a breathing circuit 101 and a patient interface 102.

The supply conduit 101 extends from an outlet in the PAP apparatus 100 and to the patient interface 102. The patient interface may be any suitable sealing patient interface such as a full face mask, nasal mask, nasal pillows, oro-nasal mask, oral mask, oral interface, nasal seal, nasal cannula or the like.

The PAP apparatus 100 comprises a blower. The blower preferably comprises a fan 103 driven by an electric motor 105. Air is drawn into the PAP apparatus 100 through the inlet 104 by the fan 103. Pressurised air leaves the fan 103 for supply to the patient. Alternatively, controllable flow generators may draw on a source of high pressure gas, and regulate a flow of gas from the high pressure source.

The PAP apparatus 100 preferably comprises a humidifier 115, as shown in the embodiment of FIG. 1. In alternative embodiments, the humidifier 115 may be separate from the PAP apparatus and part of the breathing gases supply system 1 or alternatively there may be no humidifier 115 present. The humidifier 115 as shown in FIG. 1 is a pass over type humidifier where air passing through the humidifier picks up a quantity of water vapour from a reservoir of water 107. The water reservoir 107 may be heated by a heater 108. The humidifier 115 is preferably integrated into the housing of the PAP apparatus 100. Alternatively the humidifier 115 may be a separate component within the housing of the PAP apparatus or separate from the PAP apparatus 100 with a conduit connecting between the PAP apparatus 100 and the humidifier 115. Other types of humidifiers, other than a pass over type may be used. In some forms multiple humidifiers may used in the breathing gases supply system 1.

The heater 108 and the motor 105 are supplied by a power supply (PS) 106. The amount of power supplied to the motor determines the speed the fan 103 turns at. The amount of power supplied to the heater 108 determines the amount of water vapour produced by the humidifier 115 and hence is one way of controlling the amount of humidification of the breathing gases supplied by the PAP apparatus 100. The amount of power supplied by the power supply 106 is controlled by the outputs of a controller.

The PAP apparatus comprises at least a first controller 109. The first controller 109 is used to control the blower and breathing circuit. The controller 109 may also be configured to control other components as described later. The controller 109 is supplied by power from the power supply 106. The controller receives inputs from a user interface (UI) 113. The user interface could be in the form of any suitable user interface such as a knob, a plurality of buttons, a screen or any combination thereof. The user interface 113 allows the PAP apparatus 100 to display information to the user and also allows a user to input information to the PAP apparatus, more particularly to the controller 109. The controller 109 may also be provided with an interface 114 for connecting to an external data source. The external data source may for example, be a communication interface such as a modem, or may be an interface to an external memory such as a smart card, USB, flash drive, disk drive or the like. The interface is capable of connection with a mobile storage device. For generic use, the interface 114 may be a data communications port according to any available standards for example a universal serial bus (USB) port. The interface 114 may alternatively or additionally be capable of wireless communications using any suitable technology such as RF (e.g. Bluetooth™), infrared or sonic communications technology. The interface 114 may also be capable for connecting to a wide range of peripheral devices.

The controller 109 typically comprises an embedded microcomputer with stored control programs for controlling and operation of various aspects of the PAP apparatus 100. Alternatively, the controller 109 may be removable from the PAP apparatus 100. In a further alternative form the controller 109 can be remote to the PAP apparatus 100. The controller 109 and the components of the PAP apparatus 100 and the components of the breathing gases supply apparatus 1 can be configured to communicate by wired or wireless methods.

The controller 109 preferably comprises inputs for receiving inputs from one or more sensors, which preferably comprise a flow sensor 110, a pressure sensor 111 downstream to the fan and a flow sensor 112 that is placed close to or on the patient interface to determine the flow or velocity of gases supplied to the patient or user. The flow sensor 110 may be positioned upstream or downstream to the fan 103. The sensors shown in FIG. 1 are one configuration of sensors that can be used in the breathing gases supply system 1. Any other configuration of sensors and any other types of sensors may be used. There may be fewer or more sensors than those shown in FIG. 1. There may be a variety of other sensors that measure other data such as humidity sensors, mass flow sensors, temperature sensors, EEG sensors and the like. In a preferred embodiment, as illustrated in FIG. 1, the breathing gases supply system 1 comprises a flow sensor 110, a pressure sensor 111 in the PAP apparatus 100 and a flow sensor 112 adjacent the patient interface 102. The information/data measured by the sensors, that is flow and pressure, can be referred to as breathing information/data because it relates to the breathing of the patient. The two common parameters measured are pressure and flow of gases breathed or supplied to the patient or user.

While the controller 109 might comprise a microprocessor implementing the control programs, it could alternatively comprise a programmed logic circuit (such as an FPGA) implementing the control programmed, or any other suitable implementation. Electronic circuits and logic circuits implementing the control programme may be readily devised by persons skilled in the art. The control program/controller functionality will be described later in detail with respect to FIG. 3.

Figure 2:
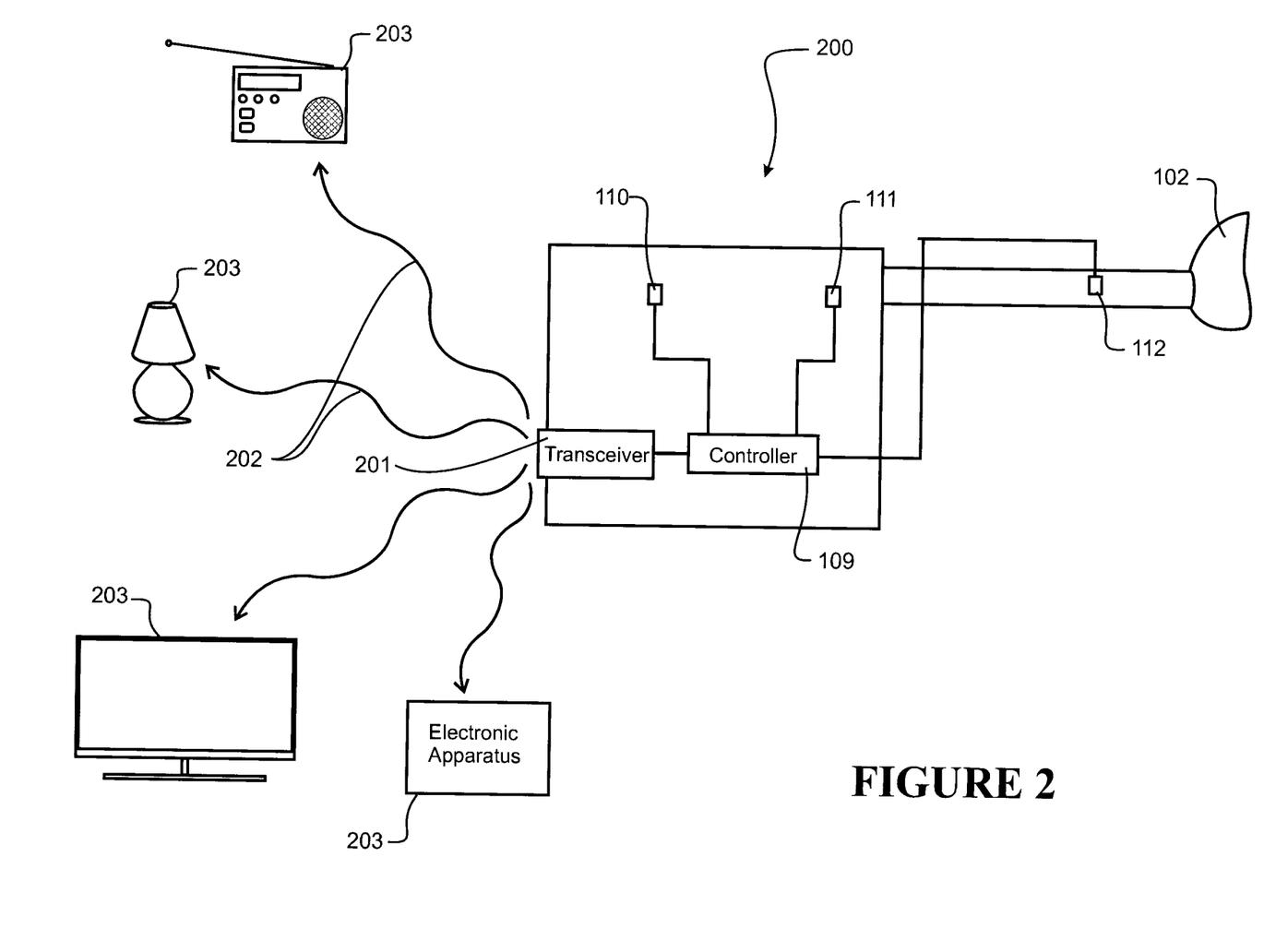
FIG. 2 is a block diagram of the control system that is part of the gas supply device that implements or performs the present invention, the figure also showing the interaction of the control system and electronic apparatuses such as appliances.

The PAP apparatus has a control system 200 configured for operating electronic apparatus 203 upon determining sleep (that is, actual sleep, onset of sleep or change in sleep state). The control system 200 can comprise a controller and other components of the PAP apparatus already described in relation to FIG. 1. FIG. 2 shows a block diagram of the control system 200 of the PAP apparatus 100 in further detail showing how it is configured to operate electronic apparatus 203 upon determining sleep in a patient.

The control system 200 comprises at least one sensor to detect/measure breathing parameters (these being sensor(s) that might already form part of the PAP apparatus), a controller for determining sleep, and a transmitter 201 operated by the control to communicate with an electronic apparatus such as a home appliance to control it upon sleep. The control system 200 preferably forms part of the breathing gases supply system 1. Preferably the control system 200 is part of the PAP apparatus 100. Alternatively only some components of the control system 200 are housed within the PAP apparatus 100 or formed integrally within the PAP apparatus 100. Some or all of the other components of the control system 200 can be positioned outside the PAP apparatus 100.

In one embodiment, as per FIG. 2, the control system 200 comprises the sensors 110, 111, 112, and the controller 109 mentioned previously. That is, the controller 109 and sensors 110, 111 and 112 that are used for the normal operation of the PAP apparatus also form part of the control system 200 for operating electronic apparatus upon determining sleep. In such an embodiment, the controller 109 receives data indicative of patient breathing from the sensors 110, 111, 112 or any other sensors and is programmed to process the data received from the sensors. The controller 109 processes the data to determine sleep in a patient based on the occurrence of SDB events detected from the received data. In particular, it is programmed to detect SDB events from the received data, and from one or more of those detected SDB events, determine patient sleep.

In this context SDB events comprise but are not limited to apneas, hypopneas, and flow limitations. The controller 109 can determine sleep by the detection of a single SDB event based on the presumption that SDB events only occur during sleeping. Alternatively, the sleep can be determined from a combination of quantitative and/or qualitative analysis of one or more detected SDB events. For example, sleep can be determined based on the: number of SDB events, duration of SDB events, spread of SDB events, and/or types of SDB events.

Alternatively, sleep can be determined by determining another breathing pattern indicative of sleep. Other sleep indicative breathing patterns are determined by measuring characteristics/parameters of breathing flow or pressure. These sleep indicative breathing patterns can be determined by, for example, measuring and processing a change in tidal volume, a reduced tidal volume, a reduced breathing rate, lack of variability in breathing or a change in the pulse rate. It should be realised breathing patterns indicative of sleep can be determined by measuring any other suitable characteristic/parameter of breathing flow or pressure besides the ones listed above.

The controller 109 can be pre-programmed during manufacture of the controller, or manufacture of the PAP apparatus 100. Alternatively the controller 109 may be programmed at a later point, by a suitable person. The program can be loaded onto the controller 109 by any suitable device or method. For example program is loaded onto the controller 109 by a mobile storage device that can be connected to the controller 109 via the interface 114. The mobile storage device may be a smart card, a micro-chip, a flash drive, a portable hard drive or any other such suitable device.

The controller 109 can be programmed with any suitable method to determine sleep and/or detect the occurrence of SDB events or other breathing pattern indicative of sleep from the sensor data. Preferably the controller 109 utilises a method that can process a variety of different input types to determine the occurrence of SDB events or other breathing pattern indicative of sleep based on the data measured by the sensors, e.g. 110, 111, and 112).

One such suitable method of determining the occurrence of an SDB event, like an apnea, hypopnoea or a flow limitation is described in U.S. patent application Ser. No. 11/198,072. U.S. patent application Ser. No. 11/198,072 describes a system that determines events by analysing the flow signal provided by a flow sensor. The system determines an apnea based on a period where the flow signal indicates a lack of patient breathing. The system determines a hypopnea based on a period of reduced breathing volume. The system determines obstructed breathing (flow limitation) on an analysis of the discrete energy spectrum of the flow signal of patient breaths. The controller 109 can implement the method or methods of determining various SDB events such as apneas, hypopneas or flow limitations, as described in U.S. patent application Ser. No. 11/198,072, the contents of which are herein incorporated by reference. Other suitable alternative methods of determining the occurrence of SDB events, such apneas, hypopneas and flow limitations can also be implemented. In alternative methods SDB events may be determined based on the changes in the pressure signal from the pressure sensor, or SDB events may be determined based on signals from any other suitable sensor. The controller 109 may implement any one method or any combination of any methods described earlier.

Alternatively, or as well as detecting SDB events, the PAP is arranged to determine other sleep indicative breathing patterns are determined by measuring characteristics/parameters of breathing flow or pressure. U.S. Pat. No. 6,988,994 describes methods for using breathing patterns to determine a patient's state, including their sleep state. This patent describes determining a regular breathing state, an SDB state and REM sleep state and a trouble wakefulness state. For example, a change from erratic to rhythmic breathing or vice versa might indicate or detection of just one of those states could be a breathing pattern indicative of sleep. Any of these breathing patterns or the states could be used to infer sleep in a patient for use in triggering control of an electronic apparatus. The contents of U.S. Pat. No. 6,988,994 are herein incorporated by reference.

The controller 109 determines the SDB event or other breathing pattern indicative of sleep for as part of its normal operation as part of the normal operation of the PAP apparatus. The breathing pattern(s) indicative of sleep are preferably also used for triggering control of other operations of the PAP apparatus during its normal used, such as for altering pressure and flow rates.

The controller 109 can also be programmed with sleep indicative breathing patterns (such as breathing pattern characteristics indicative of sleep.) The controller 109 determines breathing patterns and measures characteristics like tidal volume, variability of breathing, breath rate, pulse rate and any other suitable pattern or characteristic from the sensor data fed to the controller. The controller 109 compares the measured breathing pattern or breathing characteristics with the pre-programmed breathing patterns and determines if the measured breathing pattern is indicative of sleep. If the measured breathing pattern or breathing characteristic is identical or substantially similar to the stored sleep indicative breathing, the controller 109 determines if sleep has occurred in a patient.

In a further embodiment the controller 109 may store particular breathing characteristics indicative of sleep. Examples may be a set tidal volume, a set breathing rate, a set pulse rate, a set variability or any other suitable characteristic. The controller 109 can determine breathing characteristics from the data measured by the sensors. Once the breathing characteristics have been measured the controller 109 can check the determined breathing characteristic with the stored characteristic indicative of sleep. If the determined breathing characteristic is similar to the stored characteristic the controller 109 resolves the patient is sleeping.

The controller 109 determines the sleep based on the SDB events, or other breathing pattern of the patient indicative of sleep, or the breathing characteristics or a combination of any two or all of these parameters. The controller 109 preferably uses a combination of all three parameters to provide better accuracy to determine sleep in a patient.

The transmitter 201 of the control system 200 is connected or connectable to the controller 109 and the power supply. The controller 109 is configured to operate the transmitter 201 to send control signals generated by the controller to one or more electronic apparatus 203 to control one or more of the electronic apparatus 203. As another alternative, the transmitter 201 can produce a signal once it receives a control signal from the controller 109. The transmitter 201 communicates with electronic apparatus 203 via a suitable medium, such as: RF, Infrared, sonic/ultrasonic, using a suitable wireless protocol such as: Bluetooth™, WIFI™.

Any suitable transmitter 201 can be used with the PAP apparatus 100 and controller 109. Preferably the transmitter 201 is positioned within the PAP apparatus 100, as shown in FIGS. 1 and 2, or formed integrally into the PAP apparatus 100. Alternatively the transmitter 201 can be separate and remote to the PAP apparatus 100 and either wired to the controller 109 or alternatively wirelessly in communication with the controller 109. In another alternative, a transceiver is used instead of a transmitter. In this case, there can be two way communications between the electronic apparatus 203 and the transceiver 201, meaning the transceiver 201 can also receive signals from the electronic apparatus 203. These return signals could be related to the operation of the electronic apparatus 203.

Once the controller 109 determines sleep, it generates a control signal and operates the transmitter 201 to send the control signal to wirelessly control the operation of any electronic apparatus 203 associated with the system/PAP apparatus, as shown in FIG. 2. The control signal sent from the transmitter 201 changes the state of the electronic apparatus 203. For example, the transmitter 201 can send a signal to switch off or on appliances such as televisions, radios, electric heaters, media players or other electronic apparatus such as lights, heat pumps, air conditioners, alarm devices (such as alarm clocks) and the like. Alternatively the transmitter 201 can send a signal to change the state of the electronic apparatus 203. For example, it can reduce the volume of televisions, radios and media players, or reduce the intensity of heaters/air conditioners or dim lights. The transmitter 201 can also be configured to switch on electronic apparatus 203. The controller 109 or transmitter 201 can be configured to communicate with and control a plurality of appliances and other electronic devices simultaneously.

Method of Control

Figure 3:
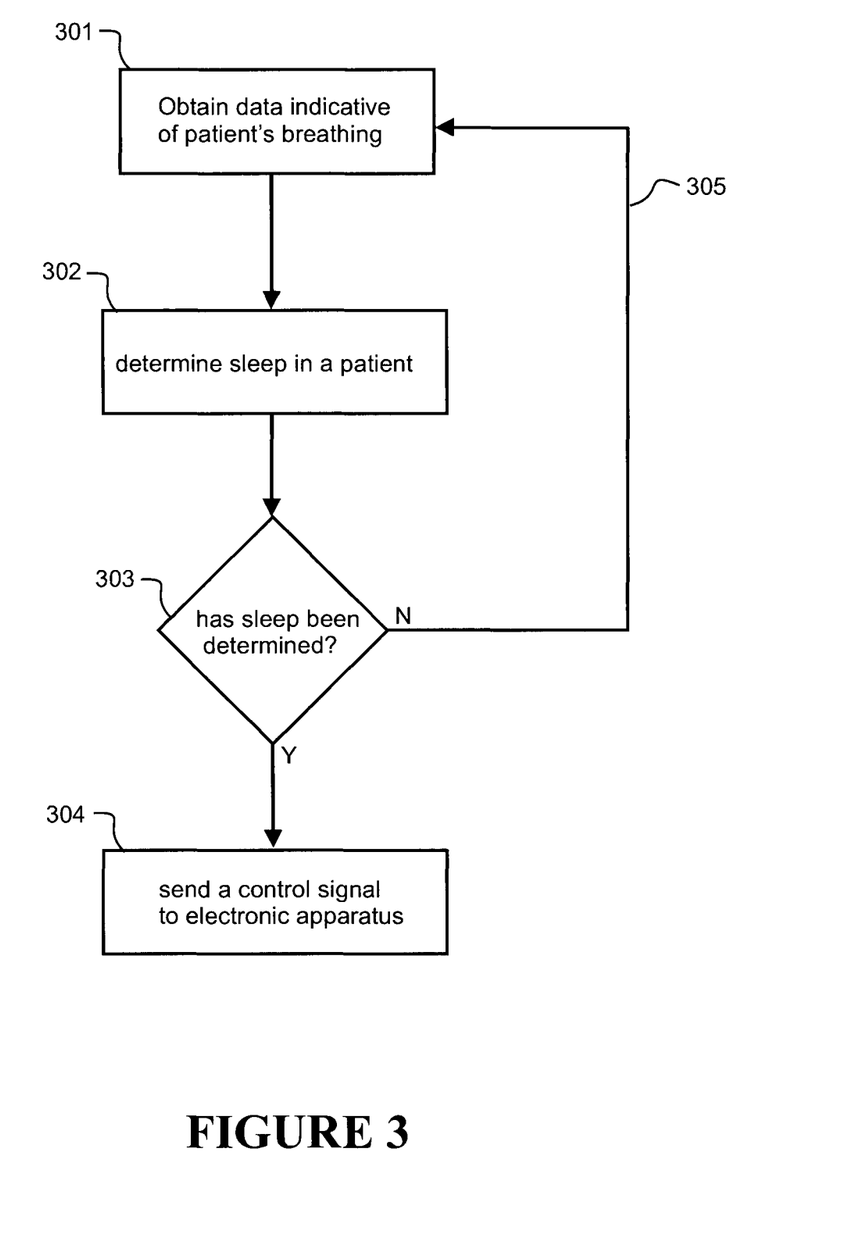
FIG. 3 is a flow diagram illustrating a control method according to the present invention which can be implemented by the controller of a gas supply device or system.

FIG. 3 shows a method for controlling electronic apparatus with a PAP apparatus 100, in particular using the control system within a PAP apparatus as per FIG. 2. The controller 109 is configured (e.g. via a program) to implement the method. In overview, the method comprises the steps of obtaining input (data/information) indicative of a patient's breathing at step 301. The next step involves determining/detecting the occurrence of SDB events or other breathing pattern indicative of sleep at step 302. Step 303 involves determining if there is sleep. Step 304 comprises sending a control signal to an electronic apparatus 203 if sleep is detected at step 303.

The method for controlling electronic apparatuses 203 using a PAP apparatus commences at step 301. At step 301 the controller 109 receives input (information/data) from the one or more sensors (e.g. 110, 111, and 112). Step 301 is periodically performed by the controller 109 at a suitable sampling rate. The sampling rate is determined by the internal clock of the controller 109 or any other clock within the PAP apparatus 100. Once data from the sensors has been received by the controller 109, the controller 109 processes the sensor data to detect the occurrence of one or more SDB events or other breathing pattern indicative of sleep at step 302. Optionally, the controller 109 uses the method or methods of determining SDB events such as apneas, hypopneas or flow limitations, as described in U.S. patent application Ser. No. 11/198,072, the contents of which are herein incorporated by reference. Any other suitable method of determining SDB events can be implemented by the controller 109. Alternatively, the controller 109 uses other methods of determining breathing patterns indicative of sleep, such as those described in U.S. Pat. No. 6,988,994.

At step 303, the controller 109 then determines sleep in a patient based on the occurrence of SDB events or other breathing pattern indicative of sleep. The controller 109 determines sleep based on any suitable relationship of SDB events or the quantitative/qualitative analysis of SDB events, or other breathing pattern indicative of sleep as described previously.

For example, in one embodiment, sleep is determined by the occurrence of a single SDB event. In other embodiments, sleep is determined based on one or more of the: number of SDB events, duration of SDB events, spread of SDB events, types of SDB events.

In a further embodiment, at step 302, the controller 109 may also or alternatively determine sleep based on the breathing pattern of the patient and whether the patient's measured breathing pattern is one that is indicative of sleep. The controller compares the measured breathing pattern or breathing characteristics with stored breathing patterns indicative of sleep, such as by using methods described in U.S. Pat. No. 6,988,994. If the measured breathing pattern is identical or similar, the controller determines the occurrence of sleep for a patient or in a patient. These breathing patterns indicative of sleep can be any one of reduced tidal volume, lack of variability, reduced breath rate or a change in pulse. The controller 109 may measure the change in breathing pattern to determine sleep. In a further embodiment the controller may also measure particular breathing characteristics that are indicative of sleep in a patient. The breathing characteristics have been explained earlier.

At step 303 the controller 109 determines sleep based on the SDB events, or the breathing pattern of the patient, or the breathing characteristics or a combination of any two or all of these parameters. The controller 109 preferably uses a combination of all three parameters to provide better accuracy to determine sleep.

The controller 109 may determine sleep based on only SDB events, other breathing patterns indicative of sleep, or a combination of SDB events and breathing pattern changes or a combination of both. The controller can implement any suitable algorithm that uses SDB event information or breathing pattern information or a combination of both to determine if sleep has occurred.

If the method determines a patient is sleeping (YES), step 303, then the method proceeds to step 304. Otherwise, the method returns to step 301 by loop 305. Loop 305 is a continuous loop and the method remains in this loop until sleep is determined at step 303.

At step 304 the controller operates the transmitter 201 to transmit the control signal to control the electronic apparatus 203 associated with the system/PAP apparatus. The method of the present invention may comprise a further step of receiving confirmation that the state of an appliance 203 has been switched. The controller can update itself or a memory element or a register within the controller memory that the electronic apparatus 203 has changed state. The controller preferably includes registers in the controller memory. The controller uses the registers to track the states of the various electronic apparatus 203 that are being controlled. The controller may be configured to determine if the electronic apparatus is ON or OFF and store the state in the register. The state may be a simple high low indicator, for example a 1 may indicate the electronic apparatus 203 is ON and a 0 may indicate the electronic apparatus 203 is off. The controller may be configured to store the state and remember the previous state of the electronic apparatus 203. The controller can be configured to only change the state of the electronic apparatus 203, by sending a control signal, if the previous state was an ON state. The controller is preferably adapted to switch the electronic apparatus 203 OFF when sleep is detected. The PAP apparatus 100 or control system 200 may also include further sensors to determine the state of the electronic apparatus 203 when the PAP apparatus is started.

The PAP apparatus 100 and method defined above is advantageous because the PAP apparatus is adapted to automatically control electronic apparatus 203 without any input from the patient or other person. The PAP apparatus 100 determines sleep, and automatically controls electronic apparatus 203 when sleep is detected. In particular the PAP apparatus 100 preferably switches off electronic devices such as televisions, radios and any other electronic apparatus. This is particularly advantageous because the patient can sleep without being disturbed by the electronic apparatus being on. The invention is also advantageous because the invention can save power by controlling the electronic apparatus 203. The PAP apparatus automatically controls electronic apparatus 203, which makes using the PAP apparatus easy for the user since there is no user input required to control the electronic apparatus. The PAP apparatus 100 and the method is advantageous because the user can remain sleeping and enjoy an undisturbed sleep because the PAP apparatus automatically controls the electronic apparatuses around the patient once sleep in a patient is detected.

Alternative Embodiments

FIG. 1 shows a one embodiment of the PAP apparatus of the present invention. There are other alternative embodiments of the PAP apparatus that are also possible. Some possible alternatives are described below.

In one alternative embodiment, the humidifier of the PAP apparatus is separate to the PAP apparatus 100. The humidifier can be positioned adjacent the PAP apparatus. In this alternative embodiment the PAP apparatus only comprises a blower, a motor, flow and pressure sensors, a user interface and a controller. The humidifier can comprise a water reservoir, a heater plate and a humidity sensor. Such a PAP system can still be part of the present invention since the controller of the PAP apparatus can be configured to control an appliance 203 or other electronic device based on determining if a person is asleep from the SDB events or the patient's other breathing patterns (such as particular breathing characteristics) indicative of sleep or a combination of these, determined from data measured by sensors.

In another alternative embodiment, the PAP apparatus comprises a plurality of controllers. In one form there is a second controller for controlling the blower and breathing circuits and the first controller can obtain data indicative of a patient's breathing, determine sleep in a patient and control the transmitter to transmit a signal to control electronic apparatus. In another alternative form there can be one controller configured to control the electric motor and the blower. Another controller can be configured to control the heater plate. A further controller can be configured to control the transmitter 201 and the power supply, with an overarching controller controlling all the sub-controllers. The controllers can also be positioned anywhere in the PAP apparatus or external to the PAP apparatus. For example the controllers can be stand alone components that communicate with each other. There are a number of other possibilities and arrangements of controllers that can be used in the PAP apparatus. The controller 109 shown is a preferred embodiment showing a general controller that controls all the functions of the PAP apparatus and is configured to implement a preferred method as per FIG. 3. Any other arrangement of controllers is also suitable for implementing the method and apparatus of the present invention and for implementing the control of electronic apparatus 203 based on SDB events or other breathing pattern indicative of sleep.

In another alternative embodiment, the controller or controllers in the PAP apparatus are removable from the PAP apparatus. In particular, the controller 109 is removable from the PAP apparatus 100. The controller 109 or controllers is removably attached, meaning the controller 109 or controllers can be removed from the PAP apparatus 100 and re-attached to PAP apparatus. This is advantageous because it allows a patient or a clinician to remove the controller to program it or troubleshoot without having to transport the whole PAP apparatus 100.

In another alternative embodiment, the PAP apparatus comprises a variety of sensors in addition to those described. Some examples are humidity sensors, mass flow sensors and sound recording sensors. The controller can be configured to determine the occurrence of SDB events or other breathing pattern indicative of sleep based on input (information/data) from any of these sensors or other sensors used.

A further alternative embodiment comprises a plurality of transmitters used with the PAP apparatus and controller 109. In one form there may a dedicated transmitter adapted to transmit a control signal to a particular appliance, for example one transmitter for a television, a separate transmitter for a radio and so on. In an alternative, the transmitter is separate to the PAP apparatus 100 and can interface with a controller 109 (or with multiple controllers) by wired or wireless methods.

In a further alternative embodiment, an algorithm is be loaded on to the controller in a variety of ways from wired connection to wireless methods. In one form, the program for determining the occurrence of SDB events or other breathing pattern indicative of sleep is programmed into the controller at manufacture and is stored in the memory of the controller. In another form, a program for the method is loaded on by a portable memory device such as a USB or flash drive. In a further alternative form, the program for the method is loaded on to the controller by wireless transmission of data from a remote server or a remote location. In a further alternative form, the controller has programs for several methods stored on it for detecting the occurrence of SDB events or other breathing patterns indicative of sleep. The method implemented by the controller depends on the type of sensors used in the PAP apparatus and the type of sensor data. The controller uses the appropriate program to process the sensor data in order to determine the occurrence of SDB events or other breathing patterns indicative of sleep.

Figure 4:
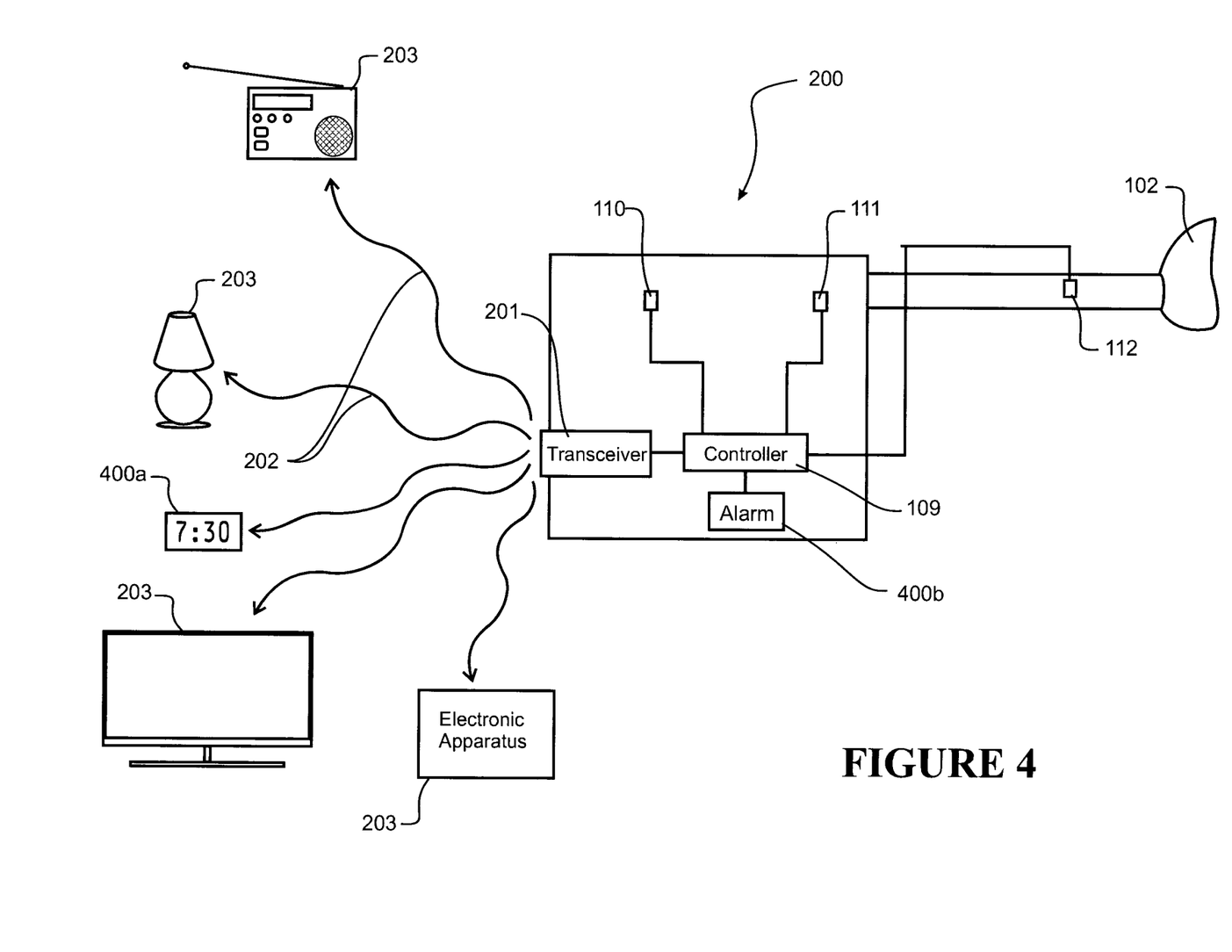
FIG. 4 is a block diagram of the control system that is part of the gas supply device that implements or performs the present invention, the figure also showing the interaction of the control system and electronic apparatuses such as appliances and alarm devices.

Referring to FIG. 4, in another embodiment the electronic apparatus is an alarm device (e.g. such as an alarm clock 400a or 400b) and the PAP apparatus 100 is configured to operate the alarm device 400a or 400b to wake up a person during a sleep state that is conducive to the patient being woken up. A patient has different sleep states. Some sleep states result in "deep sleep" (e.g. non-REM sleep) from which it is difficult to wake up from, and/or once woken up from will cause the patient to be sleepy. Alternatively, some sleep states result in "shallow sleep" (e.g. REM sleep) from which it is relatively easy for a patient to wake up. In a shallow sleep state, a patient is more conducive to being woken up. In this embodiment, the PAP apparatus 100 is configured to operate the alarm device 400a or 400b to only wake up a patient when they are in a shallow sleep state, or as close as possible in time to such a sleep state (either option being a sleep state conducive to being woken).

More particularly, the PAP apparatus control system 200 comprises an alarm device 400a or is adapted to operate a separate alarm device 400a through the controller 109. The alarm device, such as an alarm clock, can be programmed in the usual way (either directly or via the PAP apparatus 100/control system 200) to sound an alarm at a desired time (e.g. 7:30 am) to wake up a patient. This is the nominal alarm time. However, the alarm device 400a or 400b will not automatically activate the alarm at the desired/nominal time. To activate the alarm, the alarm device must receive a control signal from the PAP apparatus 100, for example via the controller 109. To do so, the PAP apparatus controller 109 monitors the time and also when the pre-programmed alarm wake up time is. In addition, the controller 109 monitors the sleep state of the patient using any of the methods described above. Once the time reaches the pre-programmed desired time, the controller 109 will only send a control signal to the alarm device 400a or 400b to activate the alarm if the patient's sleep state is one conducive to waking up (e.g. a shallow sleep state). If the sleep state is not conducive to waking up, the controller 109 will not send an alarm activation control signal to the alarm device, but rather wait until the patient has reached a sleep state conducive to waking up and then send the control signal to activate the alarm. So, for example, if at 7 am the patient is still in deep sleep state, the controller 109 will wait until it determines the patient is in a shallow sleep state and then send the activation control signal, which may for example not be until 7.15 am.

A maximum time delay could be set (by the user or manufacturer) indicating the longest time the controller 109 should delay after the nominal alarm time before sending an alarm activation control signal. After that time, the controller 109 will send an alarm activation control signal to the alarm device 400a or 400b irrespective of the patient's sleep state. This avoids the possibility that the patient will sleep too long after the desired/nominal wake up time. Alternatively, the controller could have a time window either side of the desired/nominal alarm time—e.g. 7 am+/−15 minutes, within which time the controller 109 can activate the alarm device 400a or 400b. For example, once 6.45 am is reached the controller 109 will send the alarm activation control signal to the alarm device 400a or 400b as soon as the patient reaches a shallow sleep state, and at latest by 7.15 am. A patient could set the maximum delay and/or time window.

Figure 5:
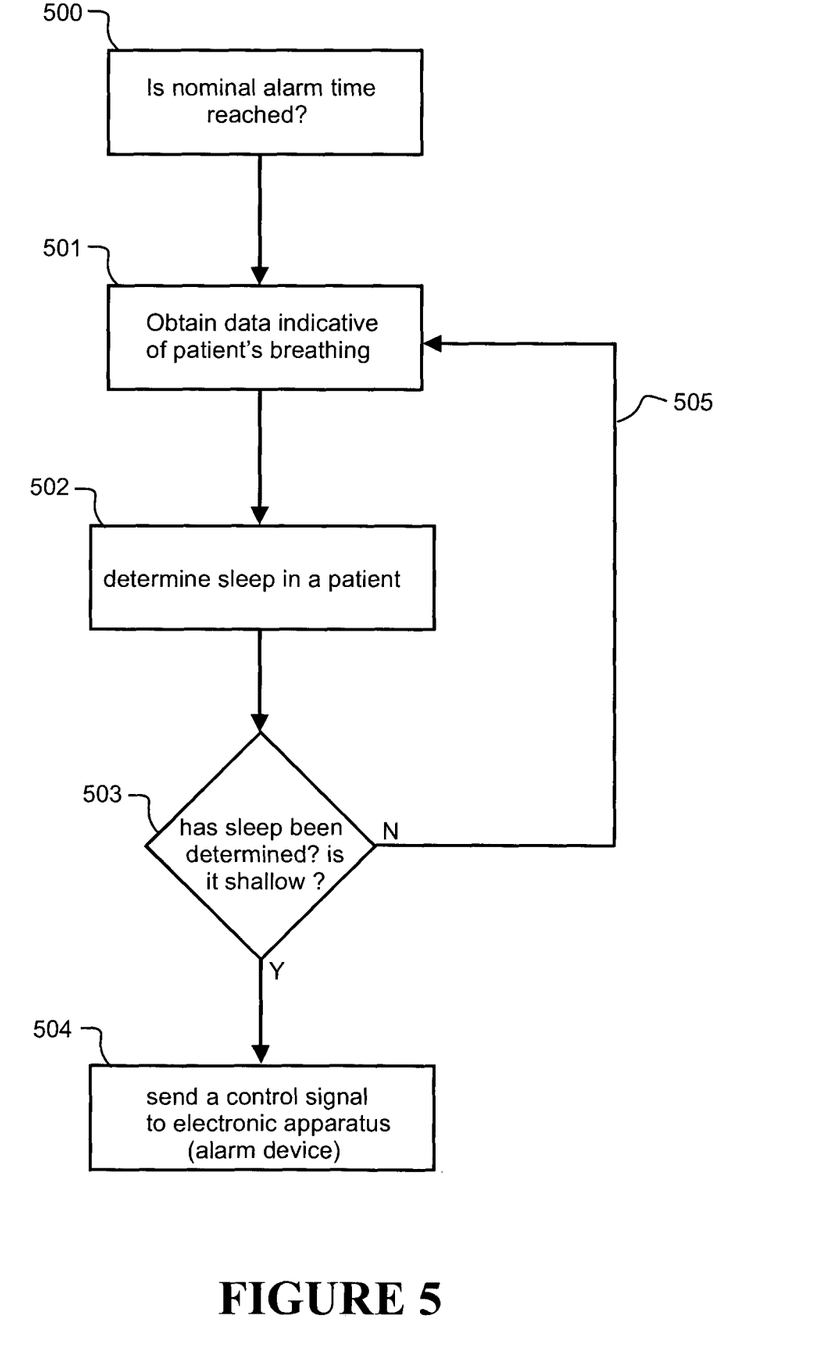
FIG. 5 is a flow diagram illustrating a control method for an alarm device according to the present invention which can be implemented by the controller of a gas supply device or system.

In summary, and with reference to FIG. 5, in the alarm embodiment the controller 109 determines if the nominal alarm time is reached, step 500. It then obtains data indicative of patient breathing, step 501 and determines the sleep state of the patient, step 502. If the sleep state is shallow, step 503, then the controller 109 sends a control signal to the alarm device 400a, or 400b, step 504. If not, the device continues to monitor the patient's breathing, step 501. The delay and/or time window could be considered also at a suitable point. It will be appreciated that this is only one embodiment and depending on time window tolerance and other factors, the order of determining sleep state and whether the correct time is reached could be reversed or they could be determined concurrently.

What is claimed is:
1. A breathing gases supply apparatus comprising:
a blower and a breathing circuit for delivering breathing gases to a patient, the blower being enclosed by a housing, a controller disposed within the housing and configured to receive input from at least one sensor indicative of patient breathing, wherein the sensor is selected from the group consisting of a pressure sensor, a flow sensor, a humidity sensor, a temperature sensor, a voltage sensor, a current sensor, an EEG sensor, and an accelerometer, a transmitter disposed within the housing and configured to communicate with the controller and transmit a control signal to remotely control an external home electronic apparatus that is an apparatus other than a breathing gases supply apparatus, the external home electronic apparatus being disposed outside of the housing and not mechanically coupled to the housing, wherein the controller is configured to determine an onset of sleep and a sleep state of the patient which is an asleep state based on the occurrence of a sleep disorder breathing (SBD) event indicative of the asleep state, detected from the input received from the sensor, and upon determining the asleep state, operate the transmitter to send the control signal to control a state of operation of the external home electronic apparatus based on the asleep state, and wherein the controller is configured to operate the transmitter to send the control signal to turn off the external home electronic apparatus or turn off a function of the external home electronic apparatus or both when the determined sleep state is the asleep state.

2. A breathing gases supply apparatus as claimed in claim 1, wherein the SDB event is one or more of a flow limitation, hypopnea or apnea.

3. A breathing gases supply apparatus as claimed in claim 1, wherein the controller is configured to determine the asleep state based on the any one or more of the following:
   number of SDB events,
   duration of SDB events,
   spread of SDB events, or
   types of SDB events.

4. A breathing apparatus as claimed in claim 1, wherein the breathing pattern indicative of the asleep state is a rhythmic or erratic breathing pattern, or a change between a rhythmic or erratic breathing pattern.

5. A breathing gases supply apparatus as claimed in claim 1, wherein the transmitter utilises infrared, RF or sonic energy to send the control signal.

6. A breathing gases supply apparatus as claimed in claim 1, wherein the external home electronic apparatus is further configured to transmit a signal to the controller and the controller further configured to receive the signal from the other external home electronic apparatus.

7. A breathing gases supply apparatus as claimed in claim 1, wherein the external home electronic apparatus is one or more of:
   a television,
   a radio
   a lights,
   a heater,
   an air conditioner,
   a heat pump,
   a media player, or
   an alarm clock.

8. A breathing gases supply apparatus as claimed in claim 1, wherein the sensor is a pressure sensor or a flow sensor.

9. A breathing gases supply apparatus as claimed in claim 1, wherein the controller is further configured to operate an alarm when the determined sleep state is a shallow sleep state or a REM sleep state.

10. A breathing gas supply apparatus as claimed in claim 9, wherein the controller is configured to operate the alarm by generating an alarm signal for controlling a state of operation of an alarm device to turn on the alarm device or an alarm function of the alarm device or both when the determined sleep state is a shallow sleep state or a REM sleep state.

11. A breathing gases supply apparatus as claimed in claim 10, wherein the alarm device is an alarm clock or other electronic apparatus.

12. A breathing gases supply apparatus as claimed in claim 11, wherein the alarm device is external to the breathing gases supply apparatus and the controller is further configured to operate the transmitter using the generated alarm signal to send a control signal to the alarm device to turn on the alarm device or the alarm function of the alarm device or both when the determined sleep state is the shallow sleep state or a REM sleep state.

13. A breathing gases supply apparatus as claimed in claim 11, wherein the alarm device is integral with the breathing gases supply apparatus.

14. A breathing gases supply apparatus comprising:
   a blower and a breathing circuit for delivering breathing gases to a patient, the blower being enclosed by a housing,
   a controller disposed within the housing and configured to receive input from at least one sensor indicative of patient breathing, wherein the controller is configured to receive an input from the sensor at a sampling rate determined by an internal clock of the controller,
   a transmitter disposed within the housing and configured to communicate with the controller and transmit a control signal to remotely control an external home electronic apparatus that is an apparatus other than the breathing gases supply apparatus, the external home electronic apparatus being disposed outside of the housing and not mechanically coupled to the housing,
   wherein the controller is configured to determine an onset of sleep and sleep in a patient based on the occurrence of a sleep disorder breathing (SBD) event indicative of sleep, detected from the input received from the sensor, and upon determining sleep, operate the transmitter to send the control signal to switch off the external home electronic apparatus.

15. A breathing gases supply apparatus as claimed in claim 14, wherein the sensor is a pressure sensor or a flow sensor.

16. A breathing gases supply apparatus as claimed in claim 14, wherein the controller is configured to determine sleep based on any one or more of the following:
   number of SDB events,
   duration of SDB events,
   spread of SDB events, or
   types of SDB events.

17. A breathing apparatus as claimed in claim 14, wherein the SBD event indicative of sleep is a rhythmic or erratic breathing pattern, or a change between a rhythmic or erratic breathing pattern.

18. A breathing gases supply apparatus as claimed in claim 14, wherein the apparatus comprises at least one sensor selected from the group consisting of:
   flow sensor,
   pressure sensor,
   humidity sensor,
   sound sensor,
   mass flow sensor,
   voltage sensor,
   current sensor,
   sensor or sensors to determine the state of the external electronic apparatus,
   EEG sensor, position sensor, and
accelerometer.

19. A breathing gases supply apparatus as claimed in claim 14, wherein the external home electronic apparatus is one or more of:
- a television,
- a radio
- a lights,
- a heater,
- an air conditioner,
- a heat pump,
- a media player, or
- an alarm clock.

* * * * *

UNITED STATES PATENT AND TRADEMARK OFFICE
CERTIFICATE OF CORRECTION

PATENT NO. : 10,828,438 B2  
APPLICATION NO. : 14/110083  
DATED : November 10, 2020  
INVENTOR(S) : James Malcolm Thompson et al.

Page 1 of 1

It is certified that error appears in the above-identified patent and that said Letters Patent is hereby corrected as shown below:

In the Specification

In Column 2, Lines 60-61, delete "accelerometer" and insert --accelerometer.--.

In Column 8, Line 40, delete "112)." and insert --112.--.

In the Claims

In Column 15, Line 14, in Claim 1, delete "(SBD)" and insert --(SDB)--.

In Column 15, Line 35, in Claim 4, delete "breathing apparatus" and insert --breathing gases supply apparatus--.

In Column 15, Line 51, in Claim 7, delete "radio" and insert --radio,--.

In Column 15, Line 64, in Claim 10, delete "gas" and insert --gases--.

In Column 16, Line 36, in Claim 14, delete "(SBD)" and insert --(SDB)--.

In Column 16, Line 51, in Claim 17, delete "breathing apparatus" and insert --breathing gases supply apparatus--.

In Column 16, Line 52, in Claim 17, delete "SBD" and insert --SDB--.

In Column 17, Line 8, in Claim 19, delete "radio" and insert --radio,--.

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*